United States Patent
Isobe et al.

(10) Patent No.: US 8,269,165 B2
(45) Date of Patent: Sep. 18, 2012

(54) NANO-ELECTROSPRAY IONIZATION TECHNIQUE AND DEVICE

(75) Inventors: Toshiaki Isobe, Tokyo (JP); Yoshio Yamauchi, Tokyo (JP)

(73) Assignee: Tokyo Metropolitan University, Tokyo (JP)

( * ) Notice: Subject to any disclaimer, the term of this patent is extended or adjusted under 35 U.S.C. 154(b) by 43 days.

(21) Appl. No.: 12/999,434

(22) PCT Filed: Jun. 2, 2010

(86) PCT No.: PCT/JP2010/059732
§ 371 (c)(1),
(2), (4) Date: Dec. 16, 2010

(87) PCT Pub. No.: WO2010/143642
PCT Pub. Date: Dec. 16, 2010

(65) Prior Publication Data
US 2011/0089319 A1    Apr. 21, 2011

(30) Foreign Application Priority Data
Jun. 8, 2009    (JP) .................................. 2009-137085

(51) Int. Cl.
*H01J 49/10* (2006.01)
(52) U.S. Cl. ...................................................... 250/288
(58) Field of Classification Search .................. 250/288, 250/281, 282
See application file for complete search history.

(56) References Cited

U.S. PATENT DOCUMENTS

| | | | | | |
|---|---|---|---|---|---|
| 5,572,023 | A | * | 11/1996 | Caprioli | 250/288 |
| 6,573,494 | B1 | * | 6/2003 | Andrien et al. | 250/288 |
| 7,015,465 | B2 | * | 3/2006 | Karol et al. | 250/288 |

FOREIGN PATENT DOCUMENTS

| | | |
|---|---|---|
| JP | 2002-015697 A | 1/2002 |
| JP | 2003-151486 A | 5/2003 |
| JP | 2005-183250 A | 7/2005 |
| JP | 2006-261116 A | 9/2006 |
| JP | 2007-1275555 A | 5/2007 |
| WO | 2006/049333 A1 | 5/2006 |
| WO | 2007/126141 A1 | 11/2007 |
| WO | 2008/087715 A1 | 7/2008 |

OTHER PUBLICATIONS

Christian G. Huber et al., Sheath liquid effect in capillary high-performance liquid chromatography-electrospray mass spectrometry of oligonucleotides, Journal of Chromatography A, 2000, pp. 413-424.
Japanese Office Action as filed in Japanese application No. 2009-137085 filed Jun. 25, 2009.
Kodama, K, et al., "A new protein engineering approach combining chemistry and biology, part I; site-specific incorporation of 4-iodo-L-phenylalanine in vitro by using misacylated suppressor tRNAPhe," Chembiochem A European Journal Of Chemical Biology, 2006, vol. 7, No. 10, pp. 1577-1581.
International Search Report for International Application No. PCT/JP2010/059732, mailed on Jul. 13, 2010.

* cited by examiner

*Primary Examiner* — Kiet T Nguyen
(74) *Attorney, Agent, or Firm* — Workman Nydegger (57) ABSTRACT

Nano-electrospray ionization techniques include the introduction of a separation solvent containing a sample to a column-integrated needle having a column filled with a resin for liquid chromatography. The separated sample components are sprayed from the tip of the column-integrated needle toward a sample introduction orifice of a mass spectrometer. An organic solvent is simultaneously introduced to a solvent-supplying needle. The organic solvent is supplied from the tip of the solvent-supplying needle to the tip of the column-integrated needle.

20 Claims, 9 Drawing Sheets

NANO-ELECTROSPRAY IONIZATION TECHNIQUE AND DEVICE

TECHNICAL FIELD

Embodiments relate to nano-electrospray ionization techniques for a mass spectrometer (MS) interface of a nano-flow liquid chromatography-mass spectrometer (LC-MS).

BACKGROUND

Since the discovery of RNA interference, it has been clarified that various types of small RNAs are deeply involved in vital activities and diseases caused by abnormalities thereof, such as cancers. Usually, a small RNA is analyzed by being converted to a cDNA with an enzyme, so-called reverse transcriptase, and then measured by a molecular biological method. Such a method has the disadvantages that analysis of chemical modification, which is important for expression of function, and quantitative measurement of the small RNA are impossible.

In known nano-LC-ESI-MS methods having the above-described restrictions, since a hydrophilic nucleotide having (−) charge is eluted from an LC column during a separation process under a low organic solvent concentration, the surface tension of the separate solution is increased. Therefore, the efficiency of ionization in a nano-electrospray ionization technique is decreased, resulting in a problem of a significant decrease in analysis sensitivity. That is, in the nano-electrospray ionization technique in which an LC separation solution having a low organic solvent concentration is used, droplets are generated at the tip of a needle for spraying the separation solution and cause clogging, which makes the spraying intermittent or discontinuous and also the analysis itself impossible.

Against these problems regarding analysis in the micro order (i.e., a flow rate of a micro-litter (μL/min) level), methods have been developed for preventing the formation of droplets at the needle tip, wherein a needle having a double-tube structure in which a "sheath tube" parallel surrounds a needle for spraying separation solution is used. The sheath tube supplies an organic solvent (sheath solution) to the LC separation solution to be sprayed (Journal of Chromatography A, 870, (2000), 413-424).

Though the above-mentioned technology is an effective method for the analysis at the micro-level, the technology has not reached a level for being applied to analysis at the nano-level (i.e., a flow rate at a nano-litter (nL/min) level). This is because that it is technically difficult to form a double-tube structure including a micro sheath tube for suitably supplying a sheath solution to a micro needle having an inner diameter of about 75 to 200 μm used in the nano-LC-ESI-MS method.

SUMMARY

According to aspects of the embodiments described herein, nano-electrospray ionization methods enable significantly high accurate mass spectrometry by stably ionizing sample components by an LC-ESI-MS method at the nano-level.

Embodiments described herein result in the prevention of the generation of droplets at the tip of a needle, which previously has made the analysis sensitivity decrease. Thus, ions can be stably formed with high efficiency, and thereby the accuracy of mass spectrometry is significantly increased by externally supplying an appropriate amount of an organic solvent to the tip of a column-integrated needle for introducing a sample with a separation solvent, separating the sample into each component, and spraying it.

According to an aspect of the nano-electrospray ionization methods, a separation solvent containing a sample is introduced to a column-integrated needle having a column filled with a resin for liquid chromatography. The separated sample components are sprayed from the tip of the column-integrated needle toward a sample introduction orifice of a mass spectrometer. Simultaneously, the organic solvent is introduced to a solvent-supplying needle and the organic solvent is supplied from the tip of the solvent-supplying needle to the tip of the column-integrated needle.

In the nano-electrospray ionization methods, the sample generally contains a small RNA.

Furthermore, in the nano-electrospray ionization methods, the flow rates of the separation solvent containing the sample and the organic solvent can each be, for example, from 50 to 500 nL/min.

Furthermore, in the nano-electrospray ionization methods, the organic solvent can be methanol, acetonitrile, or a volatile acid mixture thereof.

Furthermore, in the nano-electrospray ionization methods, the organic solvent can be mixed with nitrogen gas, and then the mixture is introduced to the solvent-supplying needle.

Furthermore, in an aspect of the nano-electrospray ionization methods, the flow rate of the nitrogen gas can be from 0.4 to 40 mL/min.

In addition, a nano-electrospray ionization device includes a column-integrated needle having a column filled with a resin for liquid chromatography and a needle is arranged to be in contact with or close to a sample introduction orifice of a mass spectrometer. A solvent-supplying needle is held on first three-dimensional positioning means that is positioned on a base table on which the column-integrated needle is positioned. The tip of the solvent-supplying needle is arranged to be in contact with or close to the tip of the column-integrated needle by driving the positioning means.

In the nano-electrospray ionization device, the column-integrated needle can be held on a second three-dimensional positioning means positioned on the base table.

Furthermore, in the nano-electrospray ionization device, the first three-dimensional positioning means can be positioned on the second three-dimensional positioning means.

Furthermore, in the nano-electrospray ionization device, the base table can be positioned near the mass spectrometer.

In another aspect, a method for performing mass spectrometry of a biological sample includes discharging, from a first needle, first droplets of a biological sample that contains nucleotide fragments. The droplets are discharged toward an orifice of a mass spectrometer. Second droplets of an organic solvent are discharged from a second needle, such that second droplets mix with the first droplets. A mixture of the first droplets and the second droplets is received at the orifice of the mass spectrometer.

According to this aspect, discharging the second droplets substantially prevents accumulation of liquid at a tip of the first needle that would otherwise disrupt the discharge of the first droplets from the first needle.

The method of performing mass spectrometry can include spectrometrically determining at least one of a type, an amount, and a chemical structure of small RNA, and the mass spectrometry can be performed as part of a method of diagnosing a disease or disorder.

In an aspect of the embodiments described herein, methods relate to the analysis of the chemical structure and function of a small RNA by directly identifying the small RNA present in a biological specimen by mass spectrometry. The small RNA as an object is cleaved with an RNase. The resulting nucleotide fragments are ionized by an electrospray ionization technique (ESI technique) while being separated by liquid chromatography (LC). The type, amount, chemical structure, and so on, of the small RNA are analyzed on the basis of an MS/MS spectrum obtained by high-performance mass spectrometry (MS) method. That is, in this so-called nano-LC-ESI-MS method, since a component in an amount of the order of fmol ($10^{-15}$ mol) is analyzed, a nucleotide fragment that is to be applied to mass spectrometry as a sample is separated by LC at an ultra-low flow rate of about 50 to 500 nL/min and then ionized as nanodroplets. Furthermore, in analysis of a phosphate group-rich small RNA, a hydrophilic nucleotide is applied, having (−) charge to mass spectrometry in the "negative mode".

According to embodiments described herein, an ultra small amount of a low-molecular-weight component can be stably ionized, and significantly high-accurate analysis can be achieved. This makes it possible to analyze a small RNA in detail and with excellent reliability, and makes it possible to highly contribute to the application of the substance to, for example, medical treatments or drugs.

DETAILED DESCRIPTION

Nano-electrospray ionization techniques according to embodiments described herein are nano-LC-ESI-MS methods for analyzing ultra small amounts of components with low molecular weights, wherein an organic solvent is supplied to the tip of an ESI needle, which sprays a sample separated by LC and ionizes the sample, from a needle other than the ESI needle.

In general, in a nano-LC-ESI-MS method, an ESI needle integrated to a column for LC can be used for minimizing, in particular, the post-column dead volume. The column-integrated needle is one in which a reversed-phase separation silica gel column having a tapering structure is filled with a resin for liquid chromatography and can immediately spray the sample components separated by the resin from the tapering column tip and form droplets of the components. The inner diameter of the narrowed tip can be designed to be about 5 to 15 μm.

In addition, the samples used in the nano-electrospray ionization techniques are not particularly limited as long as it can be used in a common nano-LC-ESI-MS method, and examples thereof include those containing, for example, protein, DNA, or RNA and mixtures thereof. According to an embodiment, a sample containing a small RNA, which have been difficult to analyze by conventional methods, can be processed. Examples of the small RNA include functional non-coding RNA (ncRNA) of about 20 to 30 nucleotides contained in a biological sample, such as microRNA or siRNA. These samples can be used for analysis by being dissolved in a buffer or salt solvent.

Figure 1:
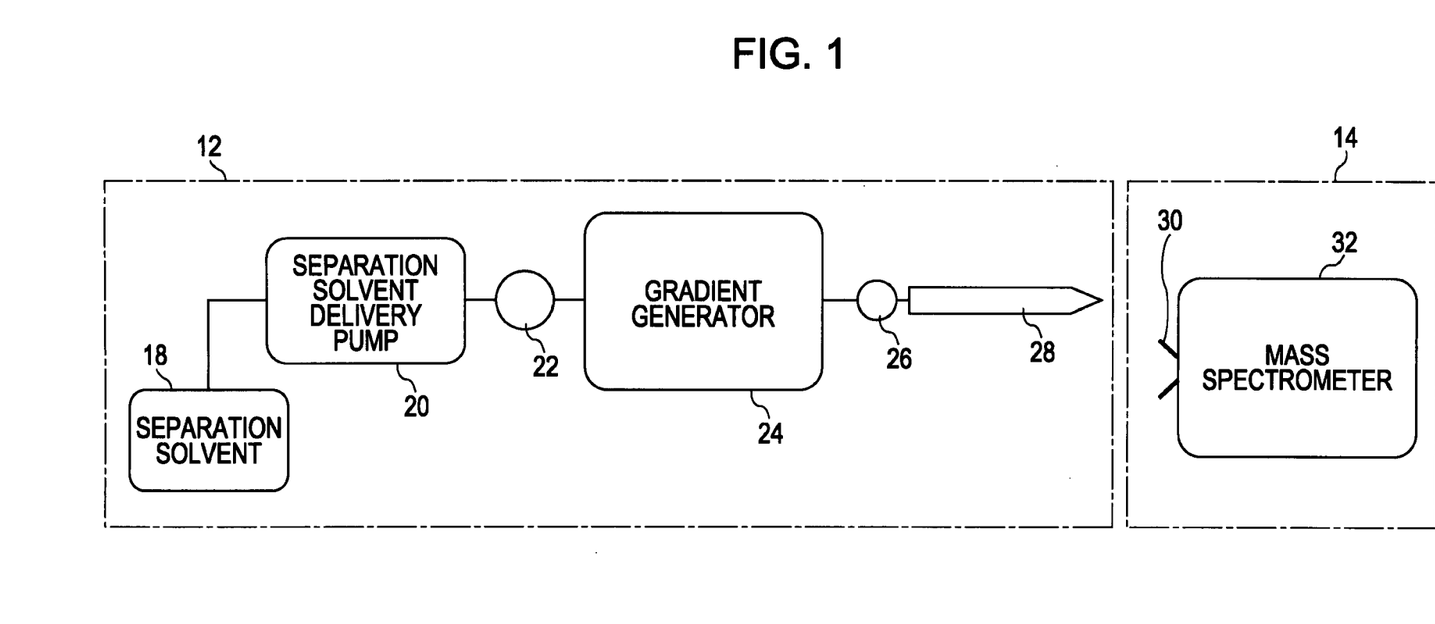
FIG. 1 is a block diagram showing a constitution of a common LC-ESI-MS.

FIG. 1 is a schematic diagram showing a constitution of a common nano-LC-ESI-MS. In FIG. 1, the nano-LC-ESI-MS includes sample-separating means 12 and mass-analyzing means 14.

The sample-separating means 12 includes a separation solvent 18, a separation solvent delivery pump 20, an injector 22, a gradient generator 24, a spray electrode 26, and a column-integrated needle 28, and these elements are properly connected to one another with flow paths. The mass-analyzing means 14 includes a sample introduction orifice 30 and a mass spectrometer 32 connected to the orifice 30. The orifice 30 is arranged so as to open toward the direction directed by the tip of the column-integrated needle 28.

In the sample-separating means 12, an analysis sample appropriately dissolved in, for example, water is sent to the gradient generator 24 by a flow of a separation solvent introduced by the injector 22 and is delivered by the separation solvent delivery pump 20 at a predetermined flow rate. The gradient generator 24 adjusts the composition and concentration of the separation solvent according to the elution characteristics of the sample components and more precisely controls the subsequent separation of the sample components in the column-integrated needle 28. In the column-integrated needle 28 having a column filled with a resin for liquid chromatography, the sample introduced with the separation solvent is separated to each component depending on the difference in hydrophilicity to the separation solvent adjusted by the gradient generator 24 and the resin. Furthermore, the column-integrated needle 28 is applied with a voltage of about −1 to −2 kV by the spray electrode 26, and the sample components separated in the column are sprayed from the tip of the column-integrated needle as charged tiny droplets in which a large number of separation solvent molecules are associated to an ion. The sample components in a droplet form are ionized by the ions inside the droplets and are introduced to the mass-analyzing means 14 through the sample introduction orifice 30 positioned in the direction directed by the needle tip.

Figure 2:
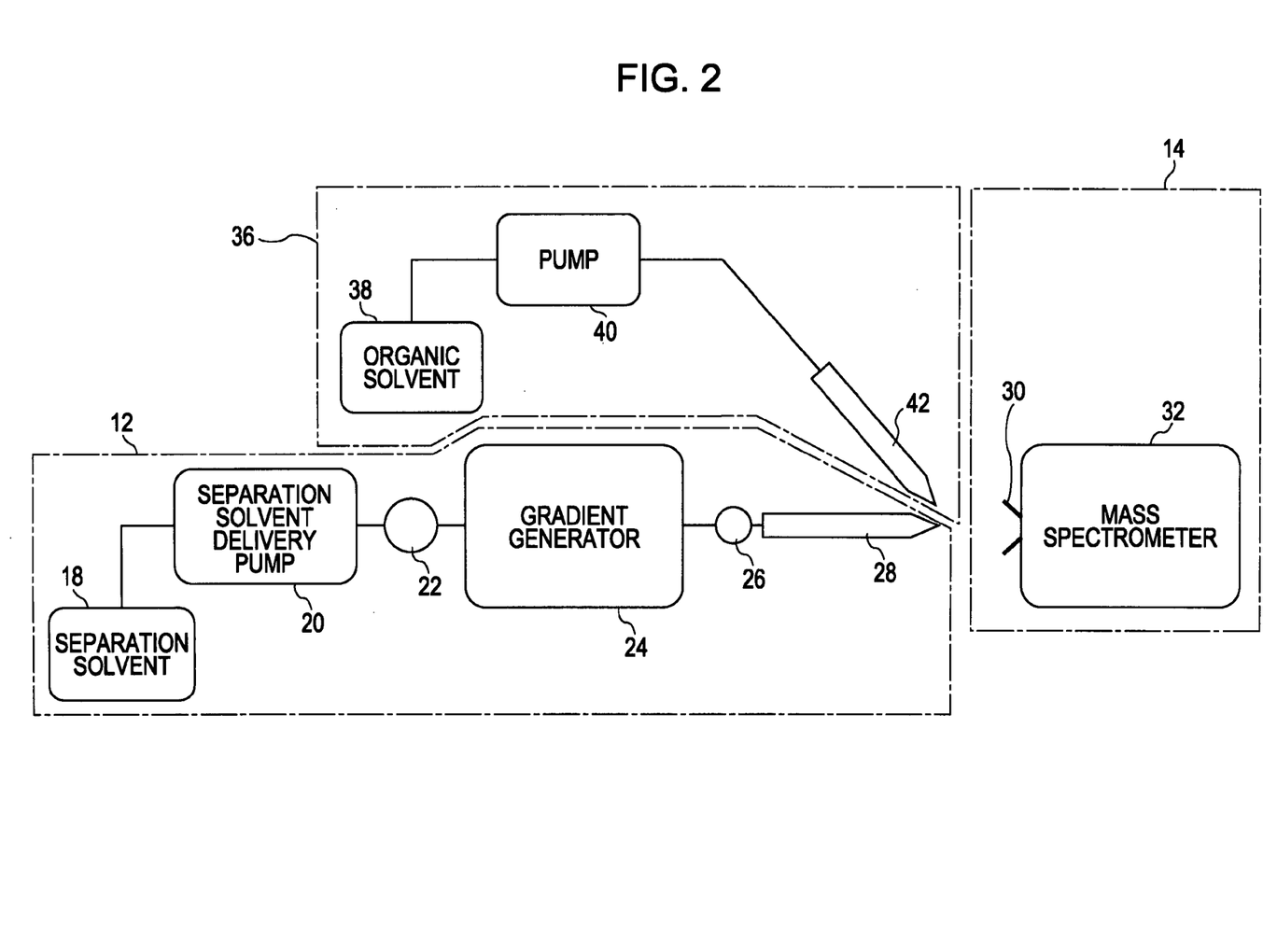
FIG. 2 is a block diagram showing a constitution of an LC-ESI-MS in a nano-electrospray ionization technique.

FIG. 2 is a schematic diagram showing a constitution in which a nano-electrospray ionization technique is introduced to the constitution of the above-described nano-LC-ESI-MS.

The nano-LC-ESI-MS shown in FIG. 2 includes solvent-supplying means 36, in addition to the sample-separating means 12 and the mass-analyzing means 14. The solvent-supplying means 36 includes an organic solvent 38, an organic solvent delivery pump 40, and a solvent-supplying needle 42, and the solvent-supplying needle 42 is positioned in such a manner that the direction of the tip of the solvent-supplying needle 42 points the tip of the column-integrated needle 28 of the sample-separating means 12.

In this constitution, the process in which a sample is introduced, separated, and then ionized for mass spectrometry is the same as that in the constitution (FIG. 1) of the above-described common nano-LC-ESI-MS.

However, in this constitution, the organic solvent 38 is delivered and introduced to the solvent-supplying needle 42 at a predetermined flow rate by the organic solvent delivery pump 40, and at the same time of the above-mentioned process, the solvent-supplying means 36 supplies the organic solvent 38 to the tip of the column-integrated needle 28 of the sample-separating means 12 from the tip of the solvent-supplying needle 42.

Figure 3:
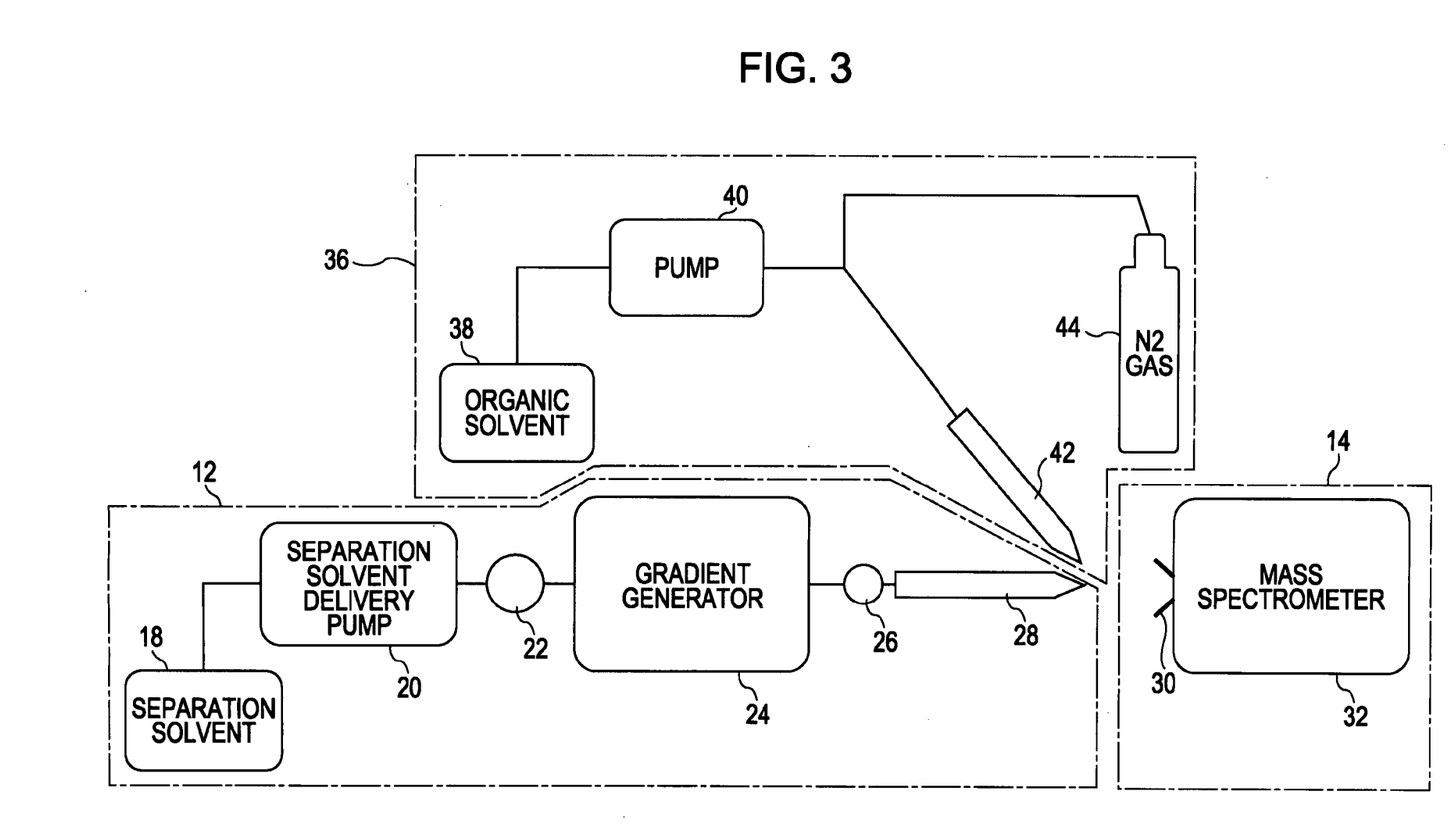
FIG. 3 is a block diagram showing a constitution of an LC-ESI-MS in a nano-electrospray ionization technique.

In another constitution shown in FIG. 3, the solvent-supplying means 36 further includes a nitrogen gas tank 44. That is, in the constitution shown in FIG. 3, the organic solvent 38 is delivered by the organic solvent delivery pump 40 and is confluent with nitrogen gas delivered from the nitrogen gas tank 44, and the solvent-supplying means 36 supplies the organic solvent 38 to the tip of the column-integrated needle 28 from the solvent-supplying needle 42 as a mixture with the nitrogen gas.

The separation solvent can be a mobile phase that is usually used in liquid chromatography (LC), and, for example, a mixture system of water or a salt solution and an organic solvent (for example, a methanol solution, an acetonitrile solution, a formic acid aqueous solution, or a triethylamine acetate aqueous solution) can be used.

Figure 4:
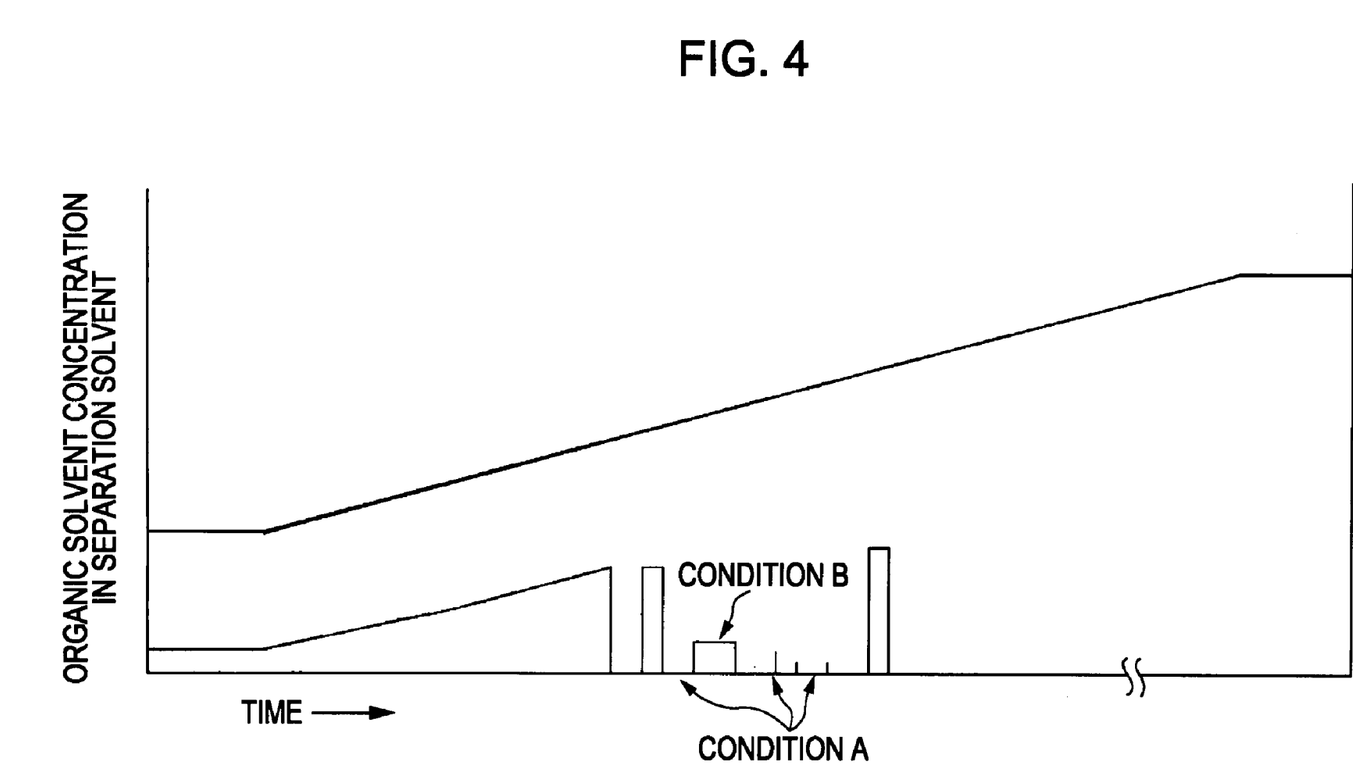
FIG. 4 is a graph showing a change (gradient) in organic solvent concentration in separation solvent in a nano-LC-ESI-MS method.

In a conventional nano-LC-ESI-MS method, since minor components contained in a sample are closely separated depending on hydrophilicity (solubility) to the organic solvent in the separation solvent, in the gradient generator 24, the composition ratio of the separation solvent is usually adjusted so as to have a gradient in which the organic solvent concentration is gradually increased from a low concentration to a high concentration. An ideal gradient line (concentration gradient of the organic solvent in the separation solvent) on this adjustment is that shown on the upper side of FIG. 4.

However, in actual measurement, in the stage where the concentration of the organic solvent in the separation solvent is low in the above-mentioned gradient, that is, in the initial stage of gradient analysis, the organic solvent concentration is low, such as several percent or less, and the droplets generated by spraying at this point are very large compared to those of the organic solvent only. Therefore, the analysis solvent in the initial stage remains at the tip of the column-integrated needle 28, due to the surface tension, and are frequently formed into droplets. Since the tip of the column-integrated needle used in nano-analysis is significantly small, if the droplets are generated, the spraying of sample components becomes intermittent (condition A) or is completely inhibited (condition B), as shown on the lower side of FIG. 4. As a result, normal analysis cannot be continued.

Accordingly, in the constitutions shown in FIGS. 2 and 3, the organic solvent is supplied to the tip, which serves as an opening for spraying the sample components, of the column-integrated needle so as to synchronize with the spraying of the sample components from the column-integrated needle, and thereby the separated sample components are diluted with the organic solvent not to remain at the opening for spraying. Thus, the generation of the droplets that prevent spraying is inhibited.

In the nano-LC-ESI-MS method including the nano-electrospray ionization shown in FIGS. 2 and 3, the sample to be introduced can advantageously be in a solution form, according to need, in which the sample is dissolved in an appropriate solvent such as water, ethanol, or acetone.

Furthermore, the flow rates of the separation solvent and the sample in the column-integrated needle 28 depend on the components of the sample and the type of the separation solvent, but can generally be 50 to 500 nL/min. In addition, the flow rate of the organic solvent supplied from the solvent-supplying needle 42 to the tip of the column-integrated needle 28 can also generally be 50 to 500 nL/min, in accordance with that of the sample solution, in order to avoid extreme dilution of the column elution solution.

Furthermore, the solvent-supplying needle 42 is not particularly limited in the material and the shape as long as it is tubular so that an organic solvent can be supplied at a very small flow rate as described above. Like the column-integrated needle, an ESI needle having a tip inner diameter of 5 to 15 μm can be advantageously used.

In addition, the organic solvent supplied from the solvent-supplying needle 42 may be any solvent that can be applied to a common liquid chromatography and can be methanol, acetonitrile, or a volatile acid (for example, formic acid or acetic acid) mixture thereof.

Furthermore, as shown in FIG. 3, when the organic solvent is mixed with nitrogen gas, the flow rate of the nitrogen gas can be, for example, 0.4 to 40 mL/min. The solvent-supplying needle in this case has an inner diameter of 30 to 75 μm, and the flow rate of the organic solvent mixed with the gas can be, for example, 50 to 500 nL/min. By supplying the nitrogen gas together with the organic solvent, the removal of the solvent from the sample components in the droplet form is accelerated, and the components are more efficiently ionized.

Figure 5:
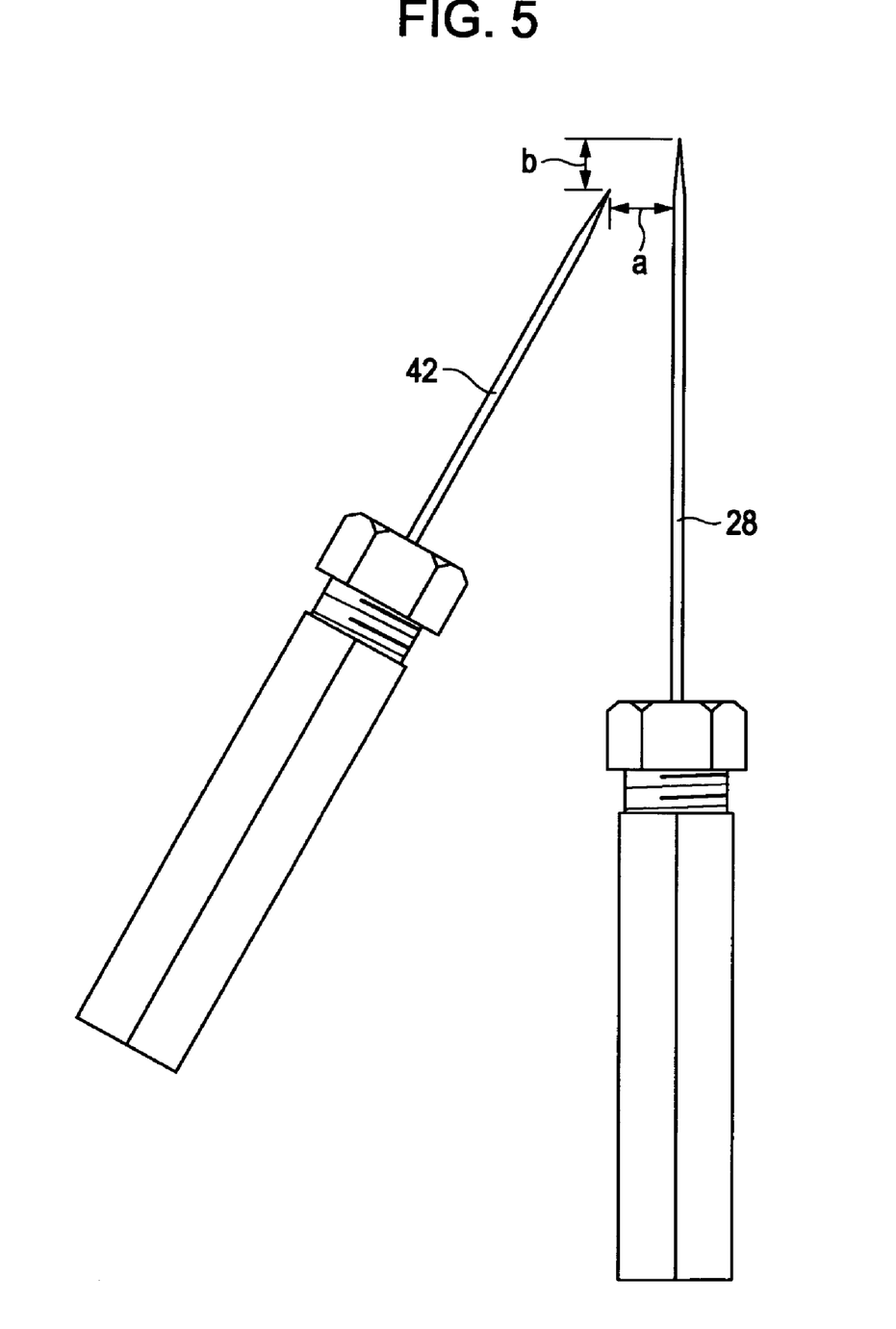
FIG. 5 is a diagram showing a distance between needles according to embodiments described herein.

Furthermore, the column-integrated needle can be arranged close to the sample introduction orifice of the mass spectrometer in a degree capable of introducing the ionized sample components and in such a manner that the needle tip faces the orifice. In addition, the solvent-supplying needle is arranged to be in contact with or close to the column-integrated needle in such a manner that the tip thereof faces the column-integrated needle. The distance (distance indicated by "a" in FIG. 5) between the column-integrated needle and the solvent-supplying needle can be, for example, about 0 to 100 μm. A distance of 0 μm refers to that the tip of the solvent-supplying needle is in contact with the column-integrated needle. A distance of 100 μm is a rough target of the distance so that the organic solvent droplets supplied from the tip of the solvent-supplying needle reach the column-integrated needle, and a more suitable distance can be appropriately adjusted within a range that the organic solvent droplets can move between the needles.

Furthermore, in usual, in the electrospray ionization using a column-integrated needle (ESI needle), droplets that prevent the sample components from being sprayed from the tip of the needle tend to be generated from a position 1 to 2 mm behind the opening for spraying. Therefore, the tip of the solvent-supplying needle can advantageously be arranged about 1 to 2 mm behind the tip of the column-integrated needle (distance indicated by "b" in FIG. 5). By arranging each needle as in above, the generation of droplets can be more reliably avoided, and normal ionization can be continued.

From the standpoint of determining needle arrangement, the nano-electrospray ionization techniques can use a nano-electrospray ionization device having positioning means for adjusting the arrangement of the column-integrated needle and the solvent-supplying needle.

That is, nano-electrospray ionization devices have a structure in which the tip of the column-integrated needle is arranged to be in contact with or close to the sample introduction orifice of the mass spectrometer and the tip of the solvent-supplying needle can be arranged to be in contact with or close to the tip of the column-integrated needle.

The nano-electrospray ionization devices will be described according to embodiments below, but are not limited thereto.

Embodiment 1

Figure 6:
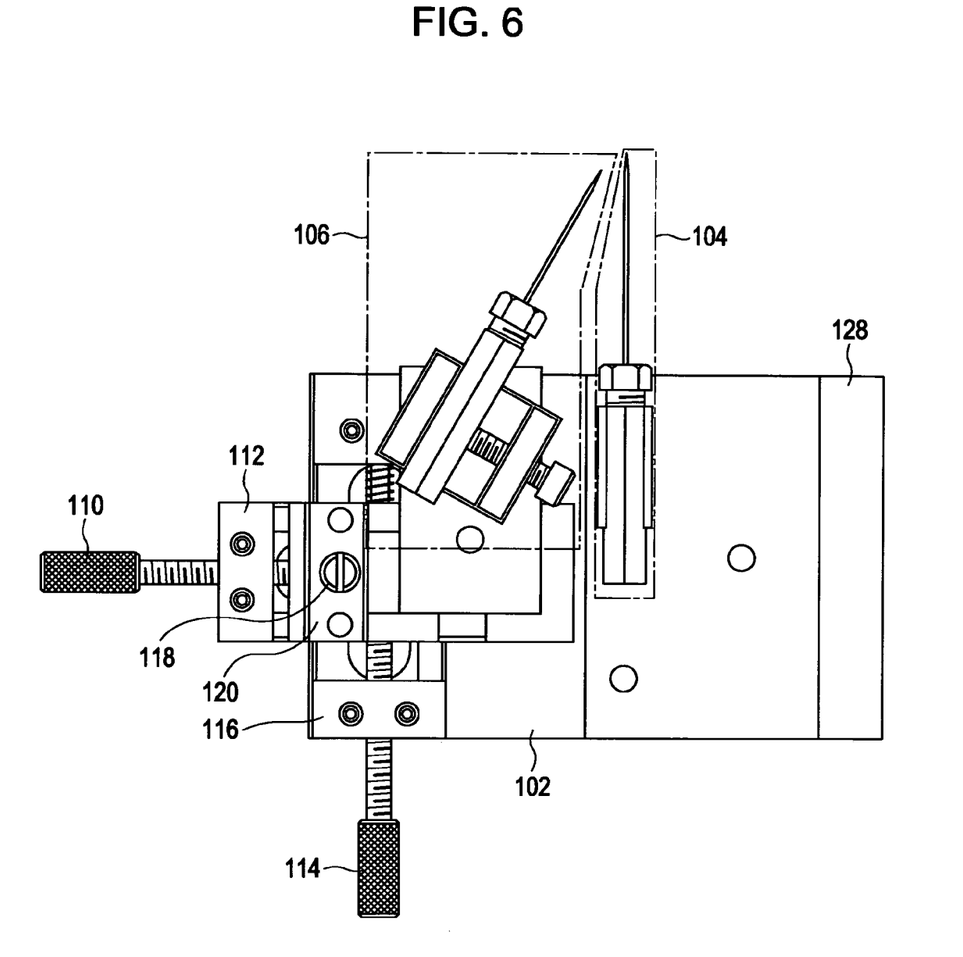
FIG. 6 is a front view of a nano-electrospray ionization device.
Figure 7:
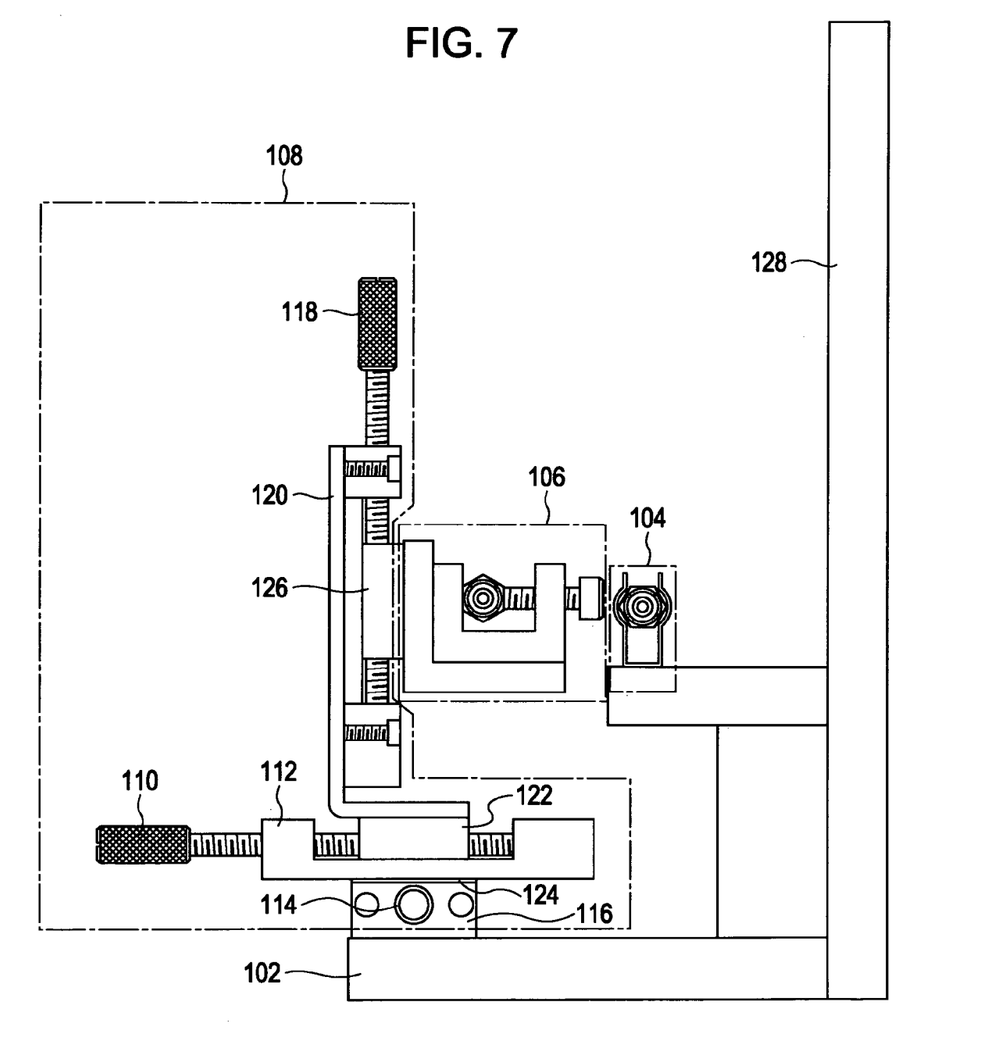
FIG. 7 is a side view of the nano-electrospray ionization device.

An embodiment of the nano-electrospray ionization devices is shown in FIG. 6 (plan view) and FIG. 7 (side view). In FIGS. 6 and 7, the device is constituted of a base table 102, column-integrated needle holding means 104, solvent-supplying needle holding means 106, three-dimensional positioning means 108. The column-integrated needle holding means 104 and the three-dimensional positioning means 108 are positioned on the base table 102, and the solvent-supplying needle holding means 106 is positioned on the three-dimensional positioning means 108.

The column-integrated needle holding means 104 can make the direction directed by the tip of the column-integrated needle held by the holding means 104 face the sample introduction orifice of the mass spectrometer.

The three-dimensional positioning means 108 is movable in the three-dimensional directions (X, Y, and Z directions) with respect to the column-integrated needle. The tip of the solvent-supplying needle held by the solvent-supplying needle holding means 106 can be arranged to be in contact with or close to the tip of the column-integrated needle by operating the means 108.

Embodiment 2

In another embodiment, the column-integrated needle holding means is held on second three-dimensional positioning means positioned on the base table. The second three-dimensional positioning means can be positioned on the base table independently from the first three-dimensional positioning means having the solvent-supplying needle holding means, or can be positioned on the base table in such a manner that the first three-dimensional positioning means and the column-integrated needle holding means are positioned on the second three-dimensional positioning means. In this embodiment, the second three-dimensional positioning means operates the tip of the column-integrated needle in the three-dimensional directions with respect to the sample introduction orifice of the mass spectrometer, and the first three-dimensional positioning means operates the tip of the solvent-supplying needle in the three-dimensional directions with respect to the tip of the column-integrated needle. Thus, the needles can be arranged to be in contact with or close to the respective object.

The structures of the first and second three-dimensional positioning means are not particularly limited as long as they can respectively control the tips of the needles positioned thereon in the three-dimensional directions with respect to the respective object. The three-dimensional positioning means 108 exemplified in FIGS. 6 and 7 is a suitable structure. In the drawings, the three-dimensional positioning means 108 includes an X-axis frame 112 fitted with an X-axis feed screw 110 in the X-axis direction, a Y-axis frame 116 fitted with a Y-axis feed screw 114 in the Y-axis direction, and a Z-axis frame 120 fitted with a Z-axis feed screw 118 in the Z-axis direction. The frames have the respective stages (122, 124, and 126) that are movable in the corresponding axis directions. By assembling these frames to be each perpendicular to the base table 102, the needle held by the means can be moved in the three-dimensional directions (X, Y, and Z directions).

Furthermore, as exemplified in FIGS. 6 and 7, it is also possible to dispose a fixing stand 128 on the base table and to fix the entire devices on the base table to the mass spectrometer through the stand. The positioning of the column-integrated needle with respect to the sample introduction orifice can be more easily performed by fixing the entire devices to be close to the sample introduction orifice.

However, when the device is fixed to the mass spectrometer, a constitution can be employed in which the three-dimensional positioning means of the solvent-supplying needle is positioned at a position apart from the mass spectrometer, as in Embodiment 1, or in which the three-dimensional positioning means of the solvent-supplying needle and the three-dimensional positioning means of the column-integrated needle are assembled to be perpendicular to each other into a single unit, as in Embodiment 2. When the three-dimensional positioning means of the solvent-supplying needle is positioned on the base table at a position near the mass spectrometer, microvibration due to, for example, the turbo pump inside the mass spectrometer is propagated to the device, and the position of the solvent-supplying needle held by the positioning means may be gradually deviated.

EXAMPLES

Nano-electrospray ionization techniques and devices therefor will be specifically shown by examples below, but are not limited thereto.

Test Example 1

Figure 8A:
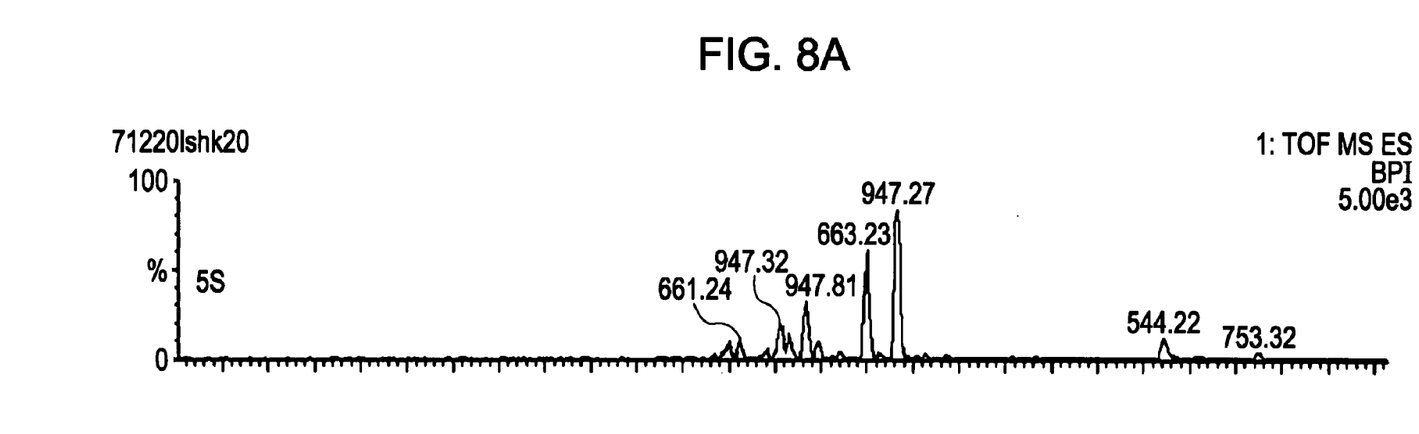
FIG. 8A is a chromatogram of RNase T1 digestion products of human 5s-rRNA determined by a nano-LC-ESI-MS method.

RNase T1 digestion products of human 5s-rRNA were analyzed using a nano-LC-ESI-MS (TOF) having a constitution shown in FIG. 2 in which the electrospray ionization device of the Embodiment 1 is connected. FIG. 8A shows the resulting chromatogram. Furthermore, FIG. 8B shows a chromatogram of the same sample by a common nano-LC-ESI-MS (TOF) having a constitution not having the solvent-supplying means as shown in FIG. 1.

The flow rate of the separation solvent containing a sample was 100 nL/min, and a mixture system of 100 nL/min of acetonitrile and 3.4 mL/min of nitrogen gas was supplied from the solvent-supplying means.

Figure 8B:
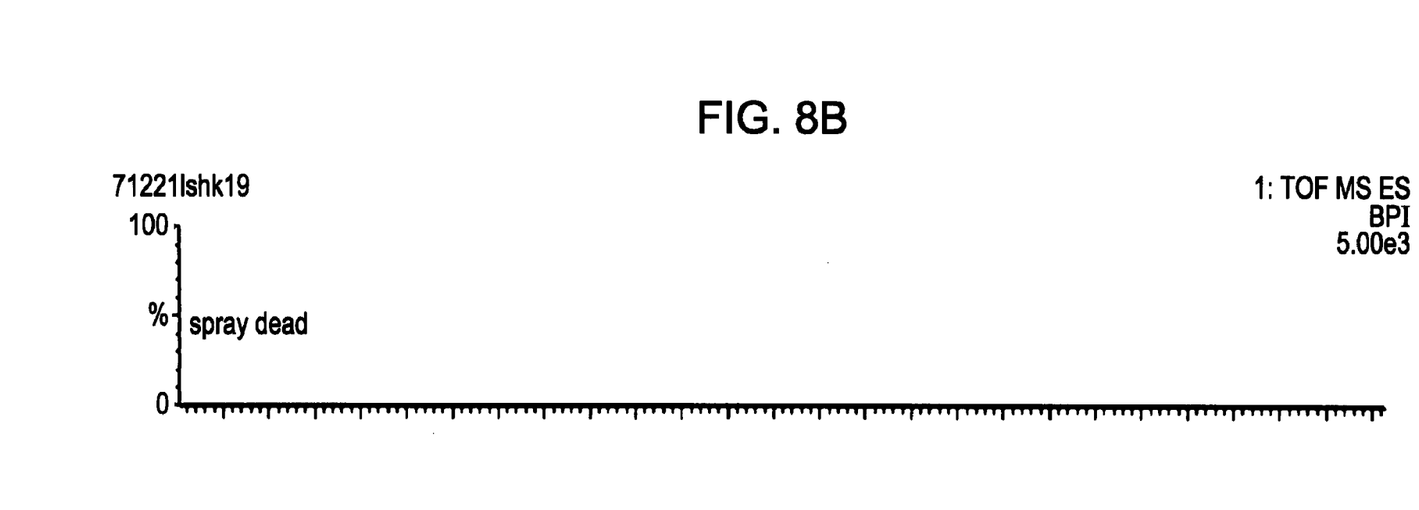
FIG. 8B is a chromatogram of RNase T1 digestion products of human 5s-rRNA determined by a conventional nano-LC-ESI-MS method.

As shown in FIGS. 8A and 8B, in the measurement (FIG. 8B) by a conventional nano-LC-ESI-MS method, droplets were generated at the tip of the needle for spraying the sample solution during the electrospray ionization process, which made the spraying impossible soon after the starting of the test, and analysis data could not be obtained.

On the other hand, in the measurement (FIG. 8A) by the nano-LC-ESI-MS method performed according to embodiments described herein, the spraying of the sample components from the column-integrated needle and the ionization stably progressed to give analysis data with high accuracy.

Test Example 2

Figure 9A:
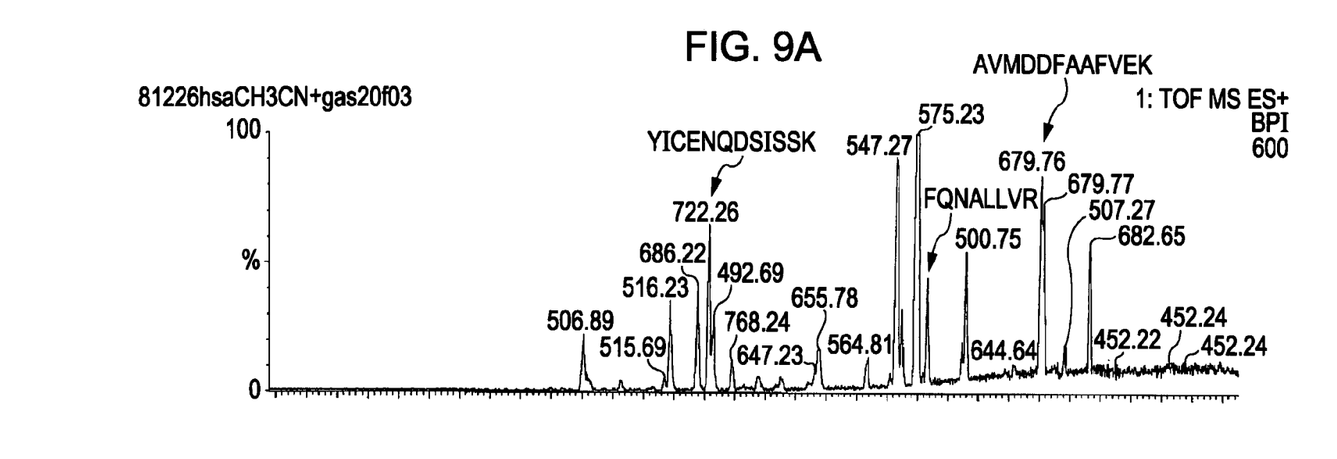
FIG. 9A is a chromatogram of trypsin digestion products of human serum albumin determined by a nano-LC-ESI-MS method.

Trypsin digestion products of human serum albumin were analyzed using the same system as that in Test Example 1. FIG. 9A shows the resulting chromatogram measured using the constitution having solvent-supplying means, and FIG. 9B shows the result by the constitution not having the solvent-supplying means.

The flow rate of the separation solvent containing a sample was 100 nL/min, and a mixture system of 100 nL/min of acetonitrile containing 0.1% formic acid and 3.4 mL/min of nitrogen gas was supplied from the solvent-supplying means.

Figure 9B:
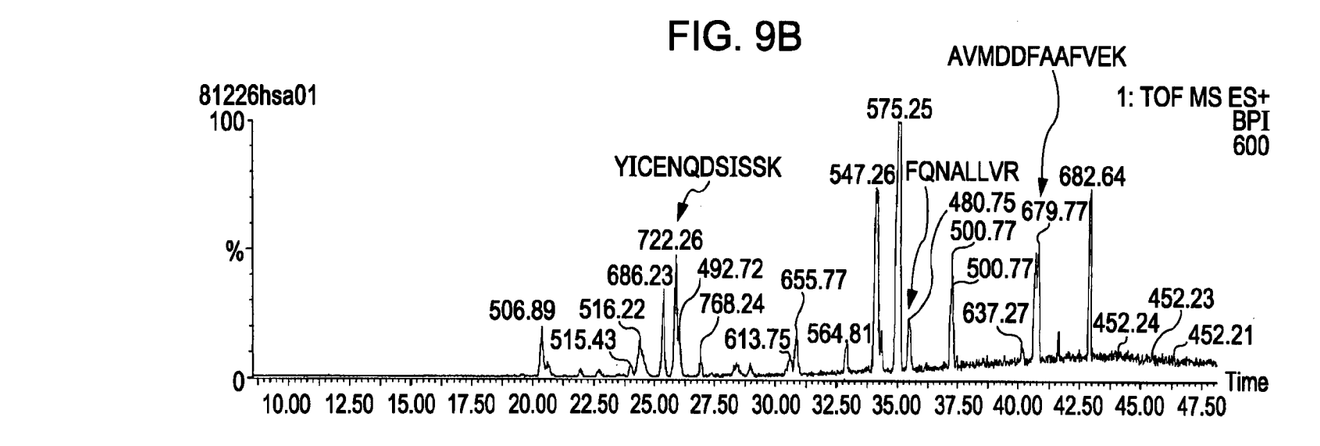
FIG. 9B is a chromatogram of trypsin digestion products of human serum albumin determined by a conventional nano-LC-ESI-MS.

As shown in FIGS. 9A and 9B, in the system (FIG. 9A) to which the nano-electrospray ionization technique and the device therefor according to embodiments described herein were applied, the analysis sensitivities for peptide components (in particular, YICENQDSISSK, FQNALLVR, and AVMDDFAAFVEK) in very small amounts were significantly high, compared to those in the system (FIG. 9B) to which the technique and the device were not applied.

The invention claimed is:

1. A method for nanoelectrospray ionization, comprising:
a first step of introducing a separation solvent comprising a sample and an organic solvent into a column-unified needle filled with a resin for liquid chromatography and spraying a separated sample component into a sample-introducing orifice of a mass spectrometer through a tip portion of the column-unified needle; and
a second step of introducing an organic solvent into a solvent-feeding needle and feeding the organic solvent to the tip portion of the column-unified needle through a tip portion of the solvent-feeding needle,
wherein a concentration of the organic solvent in the separation solvent is regulated to have a gradient of low to high, and
wherein at least in an early stage of the process in which the concentration of the organic solvent in the separation solvent is regulated to have a gradient, the first and second steps of introducings are conducted substantially simultaneously.

2. The method for nanoelectrospray ionization according to claim 1, wherein the sample comprises a low-molecular RNA.

3. The method for nanoelectrospray ionization according to claim 2, wherein the separation solvent comprising the sample and the organic solvent each have a flow rate of 50 nl/min to 500 nl/min.

4. The method for nanoelectrospray ionization according to claim 1, wherein the separation solvent comprising the sample and the organic solvent each have a flow rate of 50 nl/min to 500 nl/min.

5. The method for nanoelectrospray ionization according to claim 4, wherein the organic solvent is methanol, acetonitrile, or a volatile acid mixture thereof.

6. The method for nanoelectrospray ionization according to claim 1, wherein the organic solvent is methanol, acetonitrile, or a volatile acid mixture thereof.

7. The method for nanoelectrospray ionization according to claim 6, wherein the organic solvent is introduced into the solvent-feeding needle after mixed with a nitrogen gas.

8. The method for nanoelectrospray ionization according to claim 1, wherein the organic solvent is introduced into the solvent-feeding needle after being mixed with a nitrogen gas.

9. The method for nanoelectrospray ionization according to claim 8, wherein the nitrogen gas has a flow rate of 0.4 ml/min to 40 ml/min.

10. An apparatus for nanoelectrospray ionization, comprising:
a column-unified needle filled with a resin for liquid chromatography and in contact with or in proximity to a sample-introducing orifice of a mass spectrometer;
a solvent-feeding needle held on a first three-dimensionally positioning unit provided on the same base as that of the column-unified needle; and
a gradient generator regulating a concentration of an organic solvent in a separation solvent comprising a sample and the organic solvent to be introduced to the column-unified needle to have a gradient of low to high;
wherein a tip portion of the solvent-feeding needle can be placed in contact with or in proximity to a tip portion of the column-unified needle by utilizing the first three-dimensionally positioning unit; and
wherein at least in an early stage of regulating the concentration of the organic solvent in the separation solvent to have a gradient, the organic solvent is fed to the tip portion of the column-unified needle through the tip portion of the solvent-feeding needle.

11. The apparatus for nanoelectrospray ionization according to claim 10, wherein the column-unified needle is held on a second three-dimensionally positioning unit provided on the base.

12. The apparatus for nanoelectrospray ionization according to claim 11, which apparatus for nanoelectrospray ionization is fixed on the mass spectrometer.

13. The apparatus for nanoelectrospray ionization according to claim 11, wherein the first three-dimensionally positioning unit is provided on the second three-dimensionally positioning unit.

14. The apparatus for nanoelectrospray ionization according to claim 13, which apparatus for nanoelectrospray ionization is fixed on the mass spectrometer.

15. The apparatus for nanoelectrospray ionization according to claim 10, which apparatus for nanoelectrospray ionization is fixed on the mass spectrometer.

16. A method for nanoelectrospray ionization, comprising the steps of:
providing an apparatus for nanoelectrospray ionization, the apparatus comprising:
a column-unified needle filled with a resin for liquid chromatography and in contact with or in proximity to a sample-introducing orifice of a mass spectrometer;
a solvent-feeding needle held on a first three-dimensionally positioning unit provided on the same base as that of the column-unified needle; and
a gradient generator regulating a concentration of an organic solvent in a separation solvent comprising a sample and the organic solvent to be introduced to the column-unified needle to have a gradient of low to high;
wherein a tip portion of the solvent-feeding needle can be placed in contact with or in proximity to a tip portion of the column-unified needle by driving the first three-dimensionally positioning unit; and
wherein at least in an early stage of regulating the concentration of the organic solvent in the separation solvent to have a gradient, the organic solvent is fed to the tip portion of the column-unified needle through the tip portion of the solvent-feeding needle;
a first step of introducing a separation solvent comprising a sample and an organic solvent into the column-unified needle filled with the resin for liquid chromatography and spraying a separated sample component to a sample-introducing orifice of a mass spectrometer through the tip portion of the column-unified needle; and
a second step of introducing an organic solvent into the solvent-feeding needle and feeding the organic solvent to the tip portion of the column-unified needle through the tip portion of the solvent-feeding needle,
wherein a concentration of the organic solvent in the separation solvent is regulated to have a gradient of low to high, and
wherein at least in an early stage of the process in which the concentration of the organic solvent in the separation solvent is regulated to have a gradient, the first and second steps of introducings are conducted substantially simultaneously.

17. The method for nanoelectrospray ionization according to claim 16, wherein the method is characterized by one or more of the following:
the sample comprises a low-molecular RNA;
the separation solvent comprising the sample and the organic solvent each have a flow rate of 50 nl/min to 500 nl/min;
the organic solvent is methanol, acetonitrile, or a volatile acid mixture thereof;
the organic solvent is introduced into the solvent-feeding needle after mixed with a nitrogen gas; or
the organic solvent is introduced into the solvent-feeding needle after mixed with a nitrogen gas that has a flow rate of 0.4 ml/min to 40 ml/min.

18. The method for nanoelectrospray ionization according to claim 16, wherein the apparatus includes one or more of the following:
the column-unified needle is held on a second three-dimensionally positioning unit provided on the base; or
the first three-dimensionally positioning unit is provided on the second three-dimensionally positioning unit.

19. The method for nanoelectrospray ionization according to claim 18, wherein the method is characterized by one or more of the following:
the separation solvent comprising the sample and the organic solvent each have a flow rate of 50 nl/min to 500 nl/min;
the organic solvent is methanol, acetonitrile, or a volatile acid mixture thereof; or
the organic solvent is introduced into the solvent-feeding needle after mixed with a nitrogen gas.

20. The method for nanoelectrospray ionization according to claim 16, which apparatus for nanoelectrospray ionization is fixed on the mass spectrometer.

\* \* \* \* \*